(12) United States Patent
Goronzy et al.

(10) Patent No.: US 6,455,497 B1
(45) Date of Patent: Sep. 24, 2002

(54) METHODS AND MATERIALS FOR TREATING INFLAMMATORY DISEASES

(75) Inventors: Jorg J. Goronzy; Cornelia M. Weyand, both of Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/646,757

(22) PCT Filed: Mar. 25, 1999

(86) PCT No.: PCT/US99/06576

§ 371 (c)(1),
(2), (4) Date: Nov. 20, 2000

(87) PCT Pub. No.: WO99/48514

PCT Pub. Date: Sep. 30, 1999

(51) Int. Cl.[7] .......................... A61K 38/00; A61K 31/70
(52) U.S. Cl. .......................... 514/12; 514/44; 514/825; 514/886
(58) Field of Search .......................... 514/12, 44, 825, 514/886

(56) References Cited

U.S. PATENT DOCUMENTS

| | | | |
|---|---|---|---|
| 4,683,195 A | 7/1987 | Mullis et al. | 435/6 |
| 4,873,191 A | 10/1989 | Wagner et al. | 435/172.3 |
| 5,175,384 A | 12/1992 | Krimpenfort et al. | 800/2 |
| 5,175,385 A | 12/1992 | Wagner et al. | 800/2 |
| 5,580,859 A | 12/1996 | Felgner et al. | 514/44 |
| 5,589,466 A | 12/1996 | Felgner et al. | 514/44 |

OTHER PUBLICATIONS

Arnett, et al., *Arthritis Rheum.*, 1988, 31(3):315–324.
Brack et al., *J. Clin. Invest.*, 1997, 99(12):2842–2850.
Center et al., *Int. J. Biochem. Cell Biol.*, 1997, 29:1231–1234.
Center et al., *J. Immunol.*, 1982, 128(6):2563–2568.
Cooper et al., *Arthritis Rheum.*, 1991, 34(5):537–546.
Cruikshank et al., *J. Immunol.*, 1991, 146(9):2928–2934.
Cruikshank et al., *Proc. Natl. Acad. Sci. USA*, 1994, 91(11):5109–5113.
Feldmann et al., *Cell*, 1996, 85:307–310.
Firestein et al., *Arthritis Rheum.*, 1990, 33(6):768–773.
Gordon, *Intl. Rev. Cytol.*, 1989, 115:171–229.
Goronzy et al., *Rheum. Dis. Clin. North Am.*, 1995, 21:655–675.
Gossler et al., *Proc. Natl. Acad. Sci. USA*, 1986, 83(23):9065–9069.
Hammer et al., *Nature*, 1985, 315:680–683.
Harris Jr., *Rheumatoid Arthritis*, W.B. Saunders Company, 1997.
Kalunian et al., *Arthroscopy in "Arthritis and Allied Conditions,"* 1997, W. Koopman (Ed.), pp. 103–114.
Klimiuk et al., *Am. J. Path.*, 1997, 151(5):1311–1319.
Krimpenfort et al., *Bio/Technology*, 1991, 9:844–847.
Kurosaka et al., *J. Exp. Med.*, 1983, 158:1191–1210.
Palmiter et al., *Cell*, 1985, 41:343–345.
Pursel et al., *Science*, 1989, 244:1281–1288.
Ryan et al., *J. Biol. Chem.*, 1995, 270(29):17081–17086.
Sambrook et al., *Molecular Cloning*, 1989, 2nd Ed., Cold Spring Harbor Laboratory.
Schnieke et al., *Science*, 1997, 278:2130–2133.
Schroder et al., *Proc. Natl. Acad. Sci. USA*, 1996, 93:221–225.
Thompson et al., *Cell*, 1989, 56(2):313–321.
Van de Loo et al., *Am. J. Path.*, 1997, 151(1):177–191.
Van der Putten et al., *Proc. Natl. Acad. Sci. USA*, 1985, 82(18):6148–6152.
Weyand et al., *Arthritis Rheum.*, 1997, 40(1):19–26.

*Primary Examiner*—Kevin E. Weddington
(74) *Attorney, Agent, or Firm*—Fish & Richardson, P.C. P.A.

(57) ABSTRACT

The invention provides methods and materials related to the treatment of inflammatory diseases such as rheumatoid arthritis. Specifically, the invention provides methods and materials for treating inflammation by reducing production of an inflammatory cytokine such as IFN-γ, IL-, and TNF-α. The invention also provides methods and materials for identifying reagents that can be used to treat inflammatory diseases. Specifically, the invention provides non-human animals containing human synovial tissue as well as methods for using such non-human animals to determine the influence of various test reagents on the inflamed state of human synovial tissue.

28 Claims, 8 Drawing Sheets

METHODS AND MATERIALS FOR TREATING INFLAMMATORY DISEASES

This application is a 371 of PCT/US99/06576 filed May 25, 1999.

STATEMENT AS TO FEDERALLY SPONSORED RESEARCH

Funding for the work described herein was provided by the federal government, which may have certain rights in the invention.

BACKGROUND

1. Technical Field

The invention relates to methods and materials involved in the treatment of inflammatory disease such as rheumatoid arthritis. In addition, the invention relates to reagents that reduce inflammation as well as animal models for identifying such reagents.

2. Background Information

Rheumatoid arthritis (RA) is a systemic inflammatory disease that preferentially affects the synovial membrane and leads to irreversible damage of cartilage and bone. $CD4^+$ T cells are the dominant cell type in the inflammatory infiltrates that together with the genetic association to MHC class II molecules has been taken as evidence for a central role of T cells in the pathogenesis of the disease (Harris ED Jr, W. B. Saunders (1997)). Tissue infiltrating $CD4^+$ T cells display multiple properties suggestive for local antigen recognition, such as expression of IL-2 receptors and clonal proliferation in the joint (Goronzy J J and Weyand C M, *Rheum. Dis. Clin. North Am.* 21:655–675 (1995)). Further support for in situ T cell activation has come from the structural organization of T and B cells in the inflamed synovia. In fact, T and B cells have a tendency to form aggregates that morphologically and functionally resemble germinal centers (Kurosaka M and Ziff M, *J. Exp. Med* 158:1191–1210 (1983) and Schroder A E et al., *Pro. NatL. Acad. Sci. U.S.A.* 93:221–225 (1996)). Studies on T cell derived cytokines, however, have uniformly demonstrated that T cell products are particularly scarce in rheumatoid synovitis (Firestein G S and Zvaifler N J, *Arthritis Rheum.* 33:768–773 (1990) and Feldman M et al., *Cell* 85:307–310 (1996)). The paucity of IL-2- and interferon-γ(IFN-γ)- producing T cells in the synovial lesions has remained an enigma.

Interleukin-16 (IL-16), originally described as a lymphocyte chemoattractant factor, is a natural ligand of the CD4 molecule (Center D M and W Cruikshank, *J. Immunol.* 128:–2563–2568 (1982); Cruikshank W W et al., *J. Immunol.* 146:2929–2934 (1991); Cruikshank W W et al., *Proc. Natl. Acad. Sci. U.S.A.* 91:5109–5113 (1994); and Ryan T C et al., *J. Biol. Chem.* 270:17081–17086 (1995)). In fact, IL-16 is a pro-inflammatory cytokine that interacts with CD4 molecules and induces chemotaxis as well as IL-2 receptor and HLA-DR expression (Center D M et al., Int. *J. Biochem. Cell Biol.* 29:1231–1234 (1997)). Further, IL-16 is synthesized as a precursor protein, pro-IL-16, with $CD8^+$, but not $CD4^+$, T cells having the ability to secrete the bioactive form.

SUMMARY

The invention provides methods and materials for treating inflammatory diseases. Specifically, the invention provides methods and materials that reduce expression of an inflammatory cytokine such as IFN-γ, IL-1β, and TNF-α within inflamed tissue. For example, IL-16 polypeptide, IL-16-encoding nucleic acid, and/or an IL-16-mimicking molecule can be administered to a host such that production of an inflammatory cytokine is reduced. Alternatively, cells such as synovial tissue-derived $CD8^+$ T cells can be administered to a host containing inflamed tissue such that production of an inflammatory cytokine is reduced. It is noted that the IL-16 polypeptide, IL-16-encoding nucleic acid, IL-16-mimicking molecule, and/or cells can be administered with an immunosuppressive cytokine polypeptide, immunosuppressive cytokine-encoding nucleic acid, immunosuppressive cytokine-mimicking molecule, and/or cells expressing an immunosuppressive cytokine. Examples of immunosuppressive cytokines include, without limitation, TGF-β1, IL-4, and IL-10. The invention also provides methods and materials for identifying reagents that can be used to treat inflammatory diseases. Specifically, the invention provides non-human animals containing human synovial tissue as well as methods for using such non-human animals to determine the influence of various test reagents on the inflamed state of human synovial tissue.

One aspect of the invention features a method for treating an inflammatory disease (e.g., rheumatoid arthritis). The method includes identifying a host having inflamed tissue, and administering a pharmaceutically effective amount of an IL-16 polypeptide or an IL-16-mimicking molecule to the host under conditions such that the expression of an inflammatory cytokine (e.g., IFN-γ, IL-1β, and TNF-α) in the region of the inflamed tissue is reduced. The host is in need of an anti-inflammatory treatment and can be a mammal (e.g., a human). The IL-16 polypeptide can be recombinant human IL-16, and the IL-16-mimicking molecule can be a recombinant HIV gp120 polypeptide. The method also can include administering, to the host, a polypeptide such as TGF-β1, IL-4 and/or IL-10.

In another embodiment, the invention features a method for treating an inflammatory disease (e.g., rheumatoid arthritis) in a host. The method includes providing nucleic acid to the host. The nucleic acid encodes an IL-16 polypeptide, and the host expresses the IL-16 polypeptide from the nucleic acid such that the expression of an inflammatory cytokine (e.g., IFN-γ, IL-1β, and TNF-α) is reduced in the host. The host can be a mammal (e.g., a human). The IL-16 polypeptide can be human IL-16. The method also can include providing a second nucleic acid to the host. The second nucleic acid encodes an immunosuppressive cytokine (e.g., TGF-β1, IL-4, or IL-10).

Another embodiment of the invention features a method for treating an inflammatory disease (e.g., rheumatoid arthritis) in a host. The method includes administering, to the host, cells that reduce the expression of an inflammatory cytokine (e.g., IFN-γ, IL-1β, and TNF-α). The host can be a mammal (e.g., a human). The cells can be, for example, synovial tissue-derived $CD8^+$ T cells, cells that express IL-16 and/or TGF-α, and/or cells containing exogenous nucleic acid encoding an IL-16 polypeptide. The IL-16 can be human IL-16. The cells can contain exogenous nucleic acid that encodes a polypeptide such as TGF-β1, IL-4, and/or IL-10. In addition, the cells can have specificity for a synovial antigen, and can accumulate within synovial tissue.

In another aspect, the invention features a pharmaceutical composition for treating an inflammatory disease (e.g., rheumatoid arthritis) in a host. The composition contains an IL-16 polypeptide (e.g., recombinant human IL-16) or an IL-16-mimicking molecule (e.g., a recombinant HIV gp120 polypeptide) and an immunosuppressive cytokine (e.g., TGF-β1, IL-4, and IL-10). The administration of the composition to the host reduces the expression of an inflammatory cytokine (e.g., IFN-γ, IL-1β, and TNF-α) in the host. The host can be a mammal (e.g., a human).

Another aspect of the invention features a non-human animal containing human synovial tissue. The non-human animal can be a murine animal. In addition, the non-human animal can be immunocompromised. For example, the immunocompromised non-human animal can be a SCID mouse or a recombination-activating gene-deficient animal. At least a portion of the human synovial tissue can be located under the skin and/or in the back region of the non-human animal. The human synovial tissue can be inflamed human synovial tissue. The inflamed human synovial tissue can be in a diffuse and/or follicular state of inflammation within the animal. The human synovial tissue can be diffusely vascularized human synovial tissue within the animal. The non-human animal can be a NOD/LtSz-Prkdc$^{scid}$/J mouse having human synovial tissue derived from a rheumatoid arthritis patient.

Another aspect of the invention features a method for identifying a treatment reagent that reduces inflammation. The method includes administering a test reagent to a non-human animal having human synovial tissue, at least a portion of the human synovial tissue being inflamed, and determining if the administration of the test reagent reduces the inflammation. A reduction in inflammation indicates that the test reagent is a treatment reagent. The reduction in inflammation can be determined by measuring IFN-γ production by the human synovial tissue.

Another aspect of the invention features an article of manufacture containing packaging material and an IL-16 polypeptide or IL-16-mimicking molecule. The packaging material contains a label or package insert indicating that the IL-16 polypeptide or IL-16-mimicking molecule can be administered to a host for the purpose of treating an inflammatory disease.

In another embodiment, the invention features an article of manufacture containing packaging material and nucleic acid encoding an IL-16 polypeptide. The packaging material contains a label or package insert indicating that the nucleic acid can be administered to a host for the purpose of treating an inflammatory disease.

Another embodiment of the invention features an article of manufacture containing packaging material and cells that reduce the expression of an inflammatory cytokine. The packaging material contains a label or package insert indicating that the cells can be administered to a host for the purpose of treating an inflammatory disease.

Another aspect of the invention features the use of an IL-16 polypeptide or an IL-16-mimicking molecule in the manufacture of a medicament for treating an inflammatory disease in a host in need of an anti-inflammatory treatment. The host has inflamed tissue, and administering a pharmaceutically effective amount of the medicament to the host reduces the expression of an inflammatory cytokine in the region of the inflamed tissue.

In another embodiment, the invention features the use of a nucleic acid in the manufacture of a medicament for treating an inflammatory disease in a host in need of an anti-inflammatory treatment. The nucleic acid encodes an IL-16 polypeptide. The host has inflamed tissue, and administering the medicament to the host reduces the expression of an inflammatory cytokine in the region of the inflamed tissue.

Another embodiment of the invention features the use of cells in the manufacture of a medicament for treating an inflammatory disease in a host in need of an anti-inflammatory treatment. The host has inflamed tissue, and administering the medicament to the host reduces the expression of an inflammatory cytokine in the region of the inflamed tissue.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
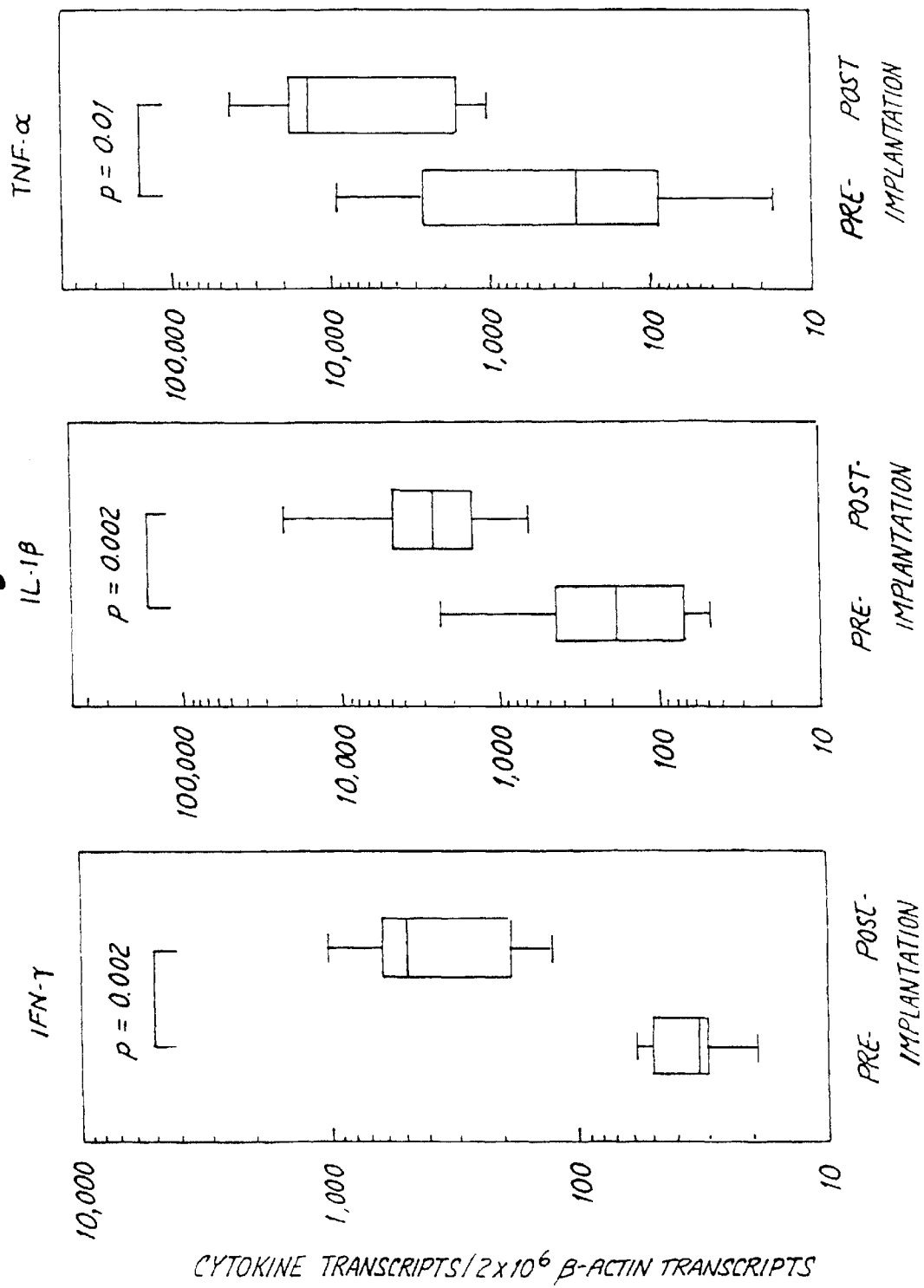
FIG. 1 contains three graphs depicting the level of cytokine mRNA production in human synovial tissue before and after implantation into severe combined immune deficient (SCID) mice.

The invention provides methods and materials related to the treatment of inflammatory diseases. Specifically, the invention provides methods and materials for treating inflammation by reducing production of an inflammatory cytokine such as IFN-γ, IL-1β, and TNF-α. Clearly, reducing the level of an inflammatory cytokine within inflamed tissue provides a useful means for treating inflammation. The invention also provides methods and materials for identifying reagents that can be used to treat inflammatory diseases. Specifically, the invention provides non-human animals containing human synovial tissue as well as methods for using such non-human animals to determine the influence of various test reagents on the inflamed state of human synovial tissue. Non-human animals containing human synovial tissue provide scientists with an invaluable tool that allows for the identification of anti-inflammatory reagents. For example, various test reagents can be administered to the living non-human animals described herein, and the reagent's influence on the state of inflammation within human tissue closely monitored. Thus, the non-human animals containing human synovial tissue described herein provide scientists with an animal model that can lead to the identification of countless different reagents that can be used to treat various forms of inflammation, including rheumatoid synovitis.

Methods and Materials for Treating Inflammation

Inflammatory diseases can be treated by administering a pharmaceutically effective amount of an IL-16 polypeptide to a host identified as being in need of anti-inflammatory treatment such that the expression of an inflammatory cytokine within inflamed tissue is reduced. The term "inflammatory disease" as used herein includes, without limitation, rheumatoid arthritis, inflammatory skin diseases such as psoriasis, inflammatory bowel diseases such as colitis, and inflammatory lung diseases such as asthma and bronchitis. Hosts in need of anti-inflammatory treatment can be identified using any medical or non-medical technique that can identify the presence of inflamed tissue. Briefly, inflamed tissues are characterized by pain, swelling, redness, and heat. Such tissue can be detected by simple observation or by the use of immuno-based diagnostic assays. For example, the presence and amount of molecules associated with inflammation such as inflammatory cytokines can be measured by enzyme-linked immunosorbant assay (ELISA) to determine if a particular tissue is inflamed. The term "inflammatory cytokine" as used herein includes, without limitation, a cytokine that stimulates an inflammatory response. Examples of inflammatory cytokines include, without limitation, IFN-γ, IL-1β, and TNF-α. The term "host" as used herein includes all animals capable of producing an inflammatory response. Thus, the term "host" includes, without limitation, mammals such as mice, rats, rabbits, sheep, goats, cows, horses, monkeys, and humans. It is noted that other molecules (e.g., anti-inflammatory agents) and/or polypeptides (e.g., immunosuppressive cytokines) in addition to IL-16 can be administered to a host such that production of an inflammatory cytokine is reduced. The term "anti-inflammatory agent" as used herein refers to compounds that counteract or suppress the inflammatory process. Examples of anti-inflammatory agents include, without limitation, glucocorticoids, anti-rejection drugs such as cyclosporin, cytotoxic agents such as cyclophosphamide, anti-metabolites such as methotrexate and azathioprine, and TNF-α receptor and IL-1 receptor antagonists. The term "immunosuppressive cytokine" as used herein refers to cytokines that reduce a host's immune response. Examples of immunosuppressive cytokines include, without limitation, TGF-β1, IL-4, and IL-10.

The term "IL-16 polypeptide" as used herein refers to any polypeptide that has an amino acid sequence similar to the amino acid sequence of recombinant human IL-16 (PeproTech, Rocky Hill, N.Y.) provided that that polypeptide can reduce production of an inflammatory cytokine within inflamed tissue. For example, such polypeptides can have the amino acid sequence of human IL-16 (accession number 1945569), mouse IL-16 (accession numbers 2911795 and 3127043), or non-human primate IL-16 (accession numbers 3127033, 3127035, 3127037, 3127039, and 3127041). It is important to note that the amino acid sequence of human IL-16 can be altered provided the altered polypeptide retains the ability to reduce production of an inflammatory cytokine. In other words, a wild-type human IL-16 polypeptide sequence can contain mutations (e.g., deletions, insertions, and substitutions as well as combinations thereof) provided the mutated form of IL-16 retains the ability to reduce production of an inflammatory cytokine. Likewise, the amino acid sequence of other polypeptides such as TGF-β1, IL-4, and IL-10 can be used in a mutated form provided at least some function of the wild-type polypeptide is maintained. It will be understood that IL-16 refers to the active form of the polypeptide, not the inactive pro-IL-16 form.

Nucleic acid that encodes a polypeptide having a wild-type or altered amino acid sequence can be identified and obtained using any method. For example, nucleic acid encoding wild-type human IL-16 can be mutated using common molecular cloning techniques (e.g., site-directed mutageneses). Again, possible mutations include, without limitation, deletions, insertions, and substitutions, as well as combinations of deletions, insertions, and substitutions. In addition, nucleic acid and amino acid databases (e.g., GenBank®) can be used to identify wild-type or altered amino acid sequences. Further, PCR and nucleic acid hybridization techniques can be used to identify nucleic acid encoding polypeptides having wild-type or altered amino acid sequences. Briefly, any nucleic acid can be used as a probe to identify a similar nucleic acid by hybridization under conditions of low to high stringency. Such similar nucleic acid then can be isolated, sequenced, and analyzed to determine the degree of alteration from a wild-type sequence.

In general, high stringency conditions can be used to identify nucleic acid having a high degree of homology to a probe. High stringency conditions can include the use of a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, and 75 mM sodium citrate at 42° C. Another example is the use of 50% formamide, 5×SSC (0.75 M NaCl, 0.075 M sodium citrate), 50 mM sodium phosphate (pH 6.5), 0.1% sodium pyrophosphate, 5×Denhardt's solution, sonicated salmon sperm DNA (50 μg/mL), 0.1% sodium lauryl sulfate (SDS), and 10% dextran sulfate at 42° C., with washes at 42° C. in 0.2×SSC and 0.1% SDS. Alternatively, low ionic strength and high temperature can be used, for washing, for example, 0.1×SSC (0.015 M NaCl/0.0015 M sodium citrate), 0.1% SDS at 65° C.

Moderate stringency conditions can be used to identify nucleic acid having a moderate degree of homology to a probe. Moderate stringency conditions can include the use of higher ionic strength and/or lower temperatures for washing of the hybridization membrane, compared to the ionic strength and temperatures used for high stringency hybridization. For example, a wash solution of 4×SSC (0.06 M NaCl/0.006 M sodium citrate), 0.1% SDS can be used at 50° C., with a last wash in 1×SSC at 65° C. Alternatively, a hybridization wash in 1×SSC at 37° C. can be used.

Low stringency conditions can be used to identify nucleic acid having a low degree of homology to a probe. Low stringency conditions can include the use of higher ionic strength and/or lower temperatures for washing of the hybridization membrane, compared to the ionic strength and temperatures used for moderate stringency hybridization. For example, a wash solution of 4×SSC (0.06 M NaCl/0.006 M sodium citrate), 0.1% SDS can be used at 37° C., with a last wash in 1×SSC at 45° C. Alternatively, a hybridization wash in 2×SSC at 37° C. can be used.

Hybridization can be done by Southern or Northern analysis to identify a DNA or RNA sequence, respectively, that hybridizes to a probe. The probe can be labeled with a radioisotope such as $^{32}P$, an enzyme, digoxygenin, or by biotinylation. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39–7.52 of Sambrook et al., (1989) Molecular Cloning, second edition, Cold Spring harbor Laboratory, Plainview, N.Y. Typically, a probe is at least about 20 nucleotides in length. In addition, probes longer or shorter than 20 nucleotides can be used.

Inflammatory diseases also can be treated by administering a pharmaceutically effective amount of an IL-16-mimicking molecule to a host identified as being in need of anti-inflammatory treatment such that the expression of an inflammatory cytokine within inflamed tissue is reduced. The term "IL-16-mimicking molecule" as used herein includes molecules that interact with CD4 and reduce production of an inflammatory cytokine. IL-16-mimicking molecules do not include IL-16 polypeptides themselves, MHC molecules, anti-CD4 antibodies, or naturally-occurring virus particles. Thus, recombinant polypeptides separated from virus particles can be IL-16-mimicking molecules. For example, recombinant HIV gp120 polypeptides can be IL-16-mimicking molecules. Again, other molecules (e.g., anti-inflammatory drugs) and polypeptides (e.g., immunosuppressive cytokines) in addition to an IL-16-mimicking molecule can be administered to a host such that production of an inflammatory cytokine is reduced.

Potential IL-16-mimicking molecules such as recombinant HIV gp120 polypeptides can be tested for the ability to specifically interact with CD4 polypeptide using methods well known in the art including, without limitation, binding assays. In addition, potential IL-16-mimicking molecules can be tested for the ability to reduce production of an inflammatory cytokine using various common methods such as RT-PCR and ELISA. When assessing the ability of an IL-16-mimicking molecule to reduce production of an inflammatory cytokine, an IL-16 polypeptide can be used as a positive control. For example, an IL-16 polypeptide and a recombinant HIV gp120 polypeptide can be used in parallel experiments to assess cytokine production within inflamed tissue.

Inflammatory diseases can be treated by providing nucleic acid that encodes an IL-16 polypeptide to a host such that IL-16 polypeptide is expressed and the production of an inflammatory cytokine within inflamed tissue is reduced. Examples of nucleic acid that encodes IL-16 polypeptides include, without limitation, human IL-16 (accession number M90391), mouse IL-16 (accession numbers AF006001 and AF017111), and non-human primate IL-16 (accession numbers AF017106, AF017107, AF017108, AF017109, and AF017110). Again, the amino acid sequence of an IL-16 polypeptide can be mutated with respect to a wild-type IL-16 polypeptide. Thus, the nucleic acid encoding an IL-16 polypeptide also can contain mutations as described herein. In addition, other molecules (e.g., anti-inflammatory drugs) and polypeptides (e.g., IL-16 and immunosuppressive cytokines) in addition to an IL-16-encoding nucleic acid can be administered to a host such that production of an inflammatory cytokine is reduced. It is noted that the provided nucleic acid would be considered exogenous to the cells within the host receiving the nucleic acid.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "exogenous" as used herein with reference to nucleic acid and a particular cell refers to any nucleic acid that does not originate from that particular cell as found in nature. Thus, all non-naturally-occurring nucleic acids are considered to be exogenous to a cell once introduced into the cell. It is important to note that non-naturally-occurring nucleic acid can contain nucleic acid sequences or fragments of nucleic acid sequences that are found in nature provided the nucleic acid as a whole does not exist in nature. For example, a nucleic acid containing a genomic DNA sequence within an expression vector is considered to be a non-naturally-occurring nucleic acid, and thus is considered to be exogenous to a cell once introduced into the cell, since that nucleic acid as a whole (genomic DNA plus vector DNA) does not exist in nature. Thus, any vector, autonomously replicating plasmid, or virus (e.g., retrovirus, adenovirus, or herpes virus) that, as a whole, does not exist in nature is considered to be a non-naturally-occurring nucleic acid. It follows that genomic DNA fragments produced by PCR or restriction endonuclease treatment as well as cDNA's are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is considered to be a non-naturally-occurring nucleic acid.

It is also important to note that a nucleic acid that is naturally-occurring can be exogenous to a particular cell. For example, an entire chromosome isolated from a cell of person X would be considered an exogenous nucleic acid with respect to a cell of person Y once that chromosome is introduced into Y's cell.

Nucleic acid encoding IL-16 or any other polypeptide can be obtained using common molecular cloning or chemical nucleic acid synthesis procedures and techniques, including PCR. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands. In addition, standard nucleic acid sequencing techniques and software programs that translate nucleic acid sequences into amino acid sequences based on the genetic code can be used to determine whether or not a particular nucleic acid has a nucleic acid sequence that encodes a particular amino acid sequence such as the amino acid sequence of IL-16.

Any method can be used to provide a host with nucleic acid. In fact, many methods for introducing nucleic acid into cells in vivo are well known to those skilled in the art. For example, lipofection and viral-mediated nucleic acid transfer are common methods for introducing nucleic acid into a host's cells. In addition, naked DNA can be delivered directly to cells in vivo as describe elsewhere (U.S. Pat. No. 5,580,859 and U.S. Pat. No. 5,589,466 including continuations thereof).

Inflammatory diseases can be treated by administering cells to a host identified as being in need of anti-inflammatory treatment such that the expression of an inflammatory cytokine within inflamed tissue is reduced. Cells that can reduce production of an inflammatory cytokine include, without limitation, cells that produce an IL-16 polypeptide. Such cells include, but are not limited to, $CD8^+/IL-16^+$ T cells as well as any cell containing an exogenous nucleic acid that encodes and expresses an IL-16 polypeptide. For example, synovial tissue-derived $CD8^+$ T cells that produce an IL-16 polypeptide can be administered to a host such that the level of an inflammatory cytokine produced within inflamed tissue is reduced. In addition, cells producing an IL-16 polypeptide can have specificity for a synovial antigen, and can accumulate within synovial tissue. Further, IL-16-producing cells can express other polypeptides in addition to IL-16. For example, $IL-16^+$ cells can express TGF-$\beta$1, IL-4, and/or IL-10. The expression of an IL-16 polypeptide as well as the expression of any additional polypeptide can be from either endogenous nucleic acid or exogenous nucleic acid that was introduced into the cell. Moreover, other molecules (e.g., anti-inflammatory agents) and/or polypeptides (e.g., immunosuppressive cytokines) can be administered to a host in addition to IL-16-producing cells.

As described herein, cells that reduce production of an inflammatory cytokine within inflamed tissue can express an IL-16 polypeptide along with other polypeptides (e.g., IL-4, IL-10, and TGF-$\beta$1). Any method can be used to identify such cells. For example, immunohistochemistry and biochemical techniques can be used to determine if a cell expresses an IL-16 polypeptide. In addition, any method can be use to make a cell express a foreign polypeptide or a polypeptide that is not normally expressed by that particular cell type. Such methods include, without limitation, constructing a nucleic acid such that a regulatory element promotes expression of a nucleic acid sequence that encodes a polypeptide. Typically, regulatory elements are DNA sequences that regulate expression of other DNA sequences at the level of transcription. Thus, regulatory elements include, without limitation, promoters, enhancers, and the like. Methods of identifying cells that express an amino acid sequence from an exogenous nucleic acid also are well known to those skilled in the art. Such methods include, without limitation, immunocytochemistry, Northern analysis, and RT-PCR.

A cell containing exogenous nucleic acid can maintain that exogenous nucleic acid in any form within the cell. For example, exogenous nucleic acid can be integrated into the genome of a cell or maintained in an episomal state. In other words, a cell used according to the invention can be a stable or transient transformant.

Any method can be used to introduce an exogenous nucleic acid into a cell. In fact, many methods for introducing nucleic acid into cells, whether in vivo or in vitro, are well known to those skilled in the art. For example, calcium phosphate precipitation, electroporation, heat shock, lipofection, microinjection, and viral-mediated nucleic acid transfer are common methods for introducing nucleic acid into cells. In addition, naked DNA can be delivered directly to cells in vivo as describe elsewhere (U.S. Pat. No. 5,580, 859 and U.S. Pat. No. 5,589,466 including continuations thereof). Further, nucleic acid can be introduced into cells by generating transgenic animals. Thus, a transgenic animal can be made to express human IL-16 so that cells from that transgenic animal can be isolated and administered to host. The administration of such cells can reduce production of an inflammatory cytokine within inflamed tissue of the host. It is noted that an IL-16 polypeptide can be isolated from transgenic animals expressing an IL-16 transgene and used as described herein. For example, a transgenic farm animal can be made to secrete IL-16 polypeptide into its milk such that large amounts can be isolated. See, e.g., Mammary Gland Transgenesis: Therapeutic Protein Production (Fidel O. Castro and Juhani Janne eds., Springer-Verlag 1997).

Transgenic animals can be aquatic animals (such as fish, sharks, dolphin, and the like), farm animals (such as pigs, goats, sheep, cows, horses, rabbits, and the like), rodents (such as rats, guinea pigs, mice, and the like), non-human primates (such as baboon, monkeys, chimpanzees, and the like), and domestic animals (such as dogs, cats, and the like). Several techniques known in the art can be used to introduce nucleic acid into animals to produce the founder lines of transgenic animals. Such techniques include, but are not limited to, pronuclear microinjection (U.S. Pat. No. 4,873, 191); retrovirus mediated gene transfer into germ lines (Van der Putten et al., *Proc. Nail. Acad. Sci., USA*, 82:6148–6152 (1985)); gene transfection into embryonic stem cells (Gossler A et al., *Proc Natl Acad Sci USA* 83:9065–9069 (1986)); gene targeting into embryonic stem cells (Thompson et al., *Cell*, 56:313–321 (1989)); nuclear transfer of somatic nuclei (Schnieke AE et al., *Science* 278:2130–2133 (1997)); and electroporation of embryos.

For a review of techniques that can be used to generate and assess transgenic animals, skilled artisans can consult Gordon (*Intl. Rev. Cytol.*, 115:171–229 (1989)), and may obtain additional guidance from, for example: Hogan et al., Manipulating the Mouse Embryo (Cold Spring Harbor Press, Cold Spring Harbor, N.Y. 1986); Krimpenfort et al., *BiolTechnology*, 9:844–847 (1991); Palmiter et al., *Cell*, 41:343–345 (1985); Kraemer et al., Genetic Manipulation of the Early Mammalian Embryo (Cold Spring Harbor Press, Cold Spring Harbor, N.Y. 1985); Hammer et al., *Nature*, 315:680–683 (1985); Purscel et al., *Science*, 244:1281–1288 (1986); Wagner et al., U.S. Pat. No. 5,175,385; and Krimpenfort et al., U.S. Pat. No. 5,175,384.

A pharmaceutically effective amount of any of the materials described herein (e.g., an IL-16 polypeptide, IL-16-mimicking molecule, IL-16-encoding nucleic acid, and IL-16-producing cell) refers to any amount that does not cause significant toxicity to the host and reduces production of an inflammatory cytokine within inflamed tissue. Such an amount can be determined by assessing the clinical symptoms associated with the inflamed tissue before and after administering a fixed amount of a particular material (e.g., an IL-16 polypeptide). In addition, the pharmaceutically effective amount of a particular material administered to a host can be adjusted according to the host's response and desired outcomes. Significant toxicity can vary for each particular patient and depends on multiple factors including, without limitation, the patient's degree of inflammation, age, and tolerance to pain.

In addition, any of the materials described herein (e.g., an IL-16 polypeptide, IL-16-mimicking molecule, IL-16-encoding nucleic acid, and IL-16-producing cell) can be administered to any part of the host's body including, without limitation, the joints, blood stream, lungs, intestines, muscle tissues, skin, peritoneal cavity, and the like. Thus, an IL-16 polypeptide can be administered by intravenous, intraperitoneal, intramuscular, subcutaneous, intrathecal, and intradermal injection, by oral administration, by inhalation, or by gradual perfusion over time. For example, an aerosol preparation containing an IL-16 polypeptide can be given to a patient by inhalation to treat, for example, lung inflammatory diseases such as asthma and bronchitis. It is noted that the duration of treatment with any of the materials described herein can be any length of time from as short as one day to as long as a lifetime (e.g., many years). For example, an IL-16 polypeptide can be administered at some frequency over a period of ten years. It is also noted that the frequency of treatment can be variable. For example, an IL-16 polypeptide can be administered once (or twice, three times, etc.) daily, weekly, monthly, or yearly.

Preparations for administration can include sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water as well as alcohol, saline, and buffered solutions. Preservatives, flavorings, and other additives such as, for example, antimicrobials, anti-oxidants, chelating agents, inert gases, and the like may also be present.

Any method can be used to determine if the expression of an inflammatory cytokine within inflamed tissue was reduced. For example, the level of expression of a particular cytokine can be determined by measuring mRNA or polypeptide levels. Thus, the amount of an inflammatory cytokine within a tissue sample can be measured using RT-PCR, functional assays (e.g., cell proliferation assays), or immunological assays (e.g., ELISA). Moreover, clinical methods that can assess the degree of inflammation can be used to determine whether inflammation in general is reduced. It is important to note that for the purpose of this invention any reduction in the degree of inflammation means that the expression of at least one inflammatory cytokine, whether currently identified or not, has been reduced.

Methods and Materials for Identifying Treatment Reagents

The invention provides non-human animals that contain human synovial tissue. Such non-human animals can maintain human synovial tissue in an inflamed state. Specifically, the human synovial tissue can remain inflamed and become diffusely vascularized after transplantation into a non-human animal such as an immunocompromised mouse (e.g., a NOD/LtSz-Prkdc$^{scid}$/J mouse). It is important to note that the inflammation observed within human synovial tissue obtained from human patients with RA is normally follicular or diffuse in nature. Follicular inflammation is characterized by the presence of T and B cells as well as dendritic cells.

In addition, tissue that is inflamed in a follicular fashion has a characteristic structure that resembles the germinal centers of lymph nodes. On the other hand, diffuse inflammation is characterized by a diffuse infiltrate of T cells and macrophages. The diffusely inflamed tissue has no real structural characteristics at the cellular level. Although not limited to any particular mode of action, it is noted that the human synovial tissue remains inflamed several months following transplantation into an immunocompromised mouse. Presumably, this means that the specific antigens and cells mediating inflammation in rheumatoid arthritis remain present and functional within the transferred synovial tissue.

The term "non-human animal" as used herein refers to all animals but humans. Thus, a non-human animal can be an aquatic animal (such as a fish, shark, dolphin, and the like), farm animal (such as a pig, goat, sheep, cow, horse, rabbit, and the like), rodent (such as a rat, guinea pig, mouse, and the like), non-human primate (such as a baboon, monkey, chimpanzee, and the like), or domestic animal (such as a dog, cat, and the like). Human synovial tissue can be obtained from human RA patients by synovial biopsy or joint surgery. See, e.g., Kalunian et al. Arthroscopy in "Arthritis and Allied Conditions" W. Koopman (Ed.) Williams and Wilkins 1997, p.103–114.

Once obtained, the human synovial tissue can be implanted into a non-human animal. Typically, immunocompromised mice are used as the non-human animals. For example, human synovial tissue is typically implanted into RAG (recombination-activating gene)-deficient or SCID mice. Normally, the human synovial tissue is implanted under the skin in the back region of the non-human animal, although any location is possible. Briefly, human synovial tissue can be cut macroscopically into pieces about three to four mm in size (e.g., about 30–60 cubic mm). The cut tissue pieces then can be implanted into immunocompromised mice such as NOD/Lt Sz-Prkdc$^{scid}$/J mice. It is noted that immunocompromised mice typically are housed in special facilities to protect them from excessive exposure to pathogens. To implant the human tissue, the mice can be anesthetized. Any method can be used to anesthetize mice, for example, methoxyflurane inhalation can be used together with an intraperitoneal administration of pentobarbital (about 50 mg/kg). For methoxyflurane inhalation, cotton lightly soaked with methoxyflurane can be placed into a syringe (e.g., a 10 cc syringe) lacking a plunger. The mouse's head then can be placed into the open end of the syringe and its breathing monitored. Typically, the mice are ready to use within five to ten minutes of constant application of methoxyflurane. Once anesthetized, the surgical area (e.g., the back region) is shaved, and a small incision is made in the skin. From this incision, a canal can be prepared under the skin by, for example, gently sliding scissors under the skin. After placing the human synovial tissue into the prepared canal, the incision is sutured and methoxyflurane inhalation removed. Typically, the mice recover within five to ten minutes of methoxyflurane removal. After implantation, the human synovial tissue can become diffusely vascularized within about seven days, and remain inflamed for many months.

The non-human animals containing human synovial tissue described herein can be used to identify treatment reagents that reduce the inflammation observed within the human synovial tissue. Specifically, a test reagent can be administered to a non-human animal having human synovial tissue, and the human synovial tissue, at least a portion of which is inflamed, can be analyzed or monitored to determine if the test reagent reduced inflammation. Test reagents can be any type of material. For example, test reagents can be, without limitation, cells, polypeptides, lipids, amino acids, nucleic acids, drugs, and chemical compounds. In addition, test reagents can be administered to any part of the non-human animal's body. For example, a test reagent can be given orally, nasally, intravenously, intraperitoneally, intramuscularly, subcutaneously, intrathecally, or intradermally. In addition, a test reagent can be directly administered to the inflamed human synovial tissue within the non-human animal. It is noted that a test reagent can be administered at any dose, for any duration, and at any frequency. Further, any method can be used to determine if a particular test reagent reduced inflammation. For example, the production of an inflammatory cytokine within the inflamed tissue can be measured to determine whether the inflammatory state of the human synovial tissue has been reduced.

The invention will be further described in the following examples, which do not limit the scope of the invention described in the claims.

EXAMPLES

Example 1—Generation of Non-human Animal Containing Human Synovium (human synovium-SCID mouse chimeras)

1. Study Population and Source of Human Synovial Tissue

Synovial tissue from synovial biopsy or joint surgery was obtained from eleven patients with active RA. Each patient fulfilled the ACR 1987 revised criteria for RA (Arnett F. C., et al., *Arthritis Rheum.* 31:315–324 (1988)). The mean age was 60 years (range 41–75 years) and the mean disease duration was 23 years (range 4–51 years). All patients had active synovitis at the time of tissue collection, and histology of the synovial tissue revealed dense mononuclear cell infiltrates. Seven patients had rheumatoid factor. Four of the eleven patients had been treated with only nonsteroidal anti-inflammatory drugs (NSAIDs) for at least three months prior to surgery. The remaining seven patients were treated with low-dose corticosteroids (n=4), hydroxychloroquine (n=2), and/or methotrexate (n=3). All patients were typed for their HLA-DRB1 alleles by PCR and subsequent oligonucleotide hybridization (Biotest Diagnostics, Danville, N.J.). Eight patients contained the disease-associated allele designated HLA-DRB1*04, while two patients contained the HLA-DRB1*01 allele.

2. Generation of Human Synovium-SCID Mouse Chimeras

To generate an in vivo model for human rheumatoid synovitis, human synovial tissue was collected and implanted into immunocompromised mice. In preliminary studies, the recipient mouse strain, the size of the graft, and the implantation site were found to be critical in providing optimal conditions for the persistence of inflammatory lesions within the engrafted tissue. When synovial tissue from a patient with active synovitis was engrafted subcutaneously in the lower back region of NOD-SCID mice, synovitis persisted at least two months. Full engraftment of the tissue was usually achieved five to seven days following transplantation, and was associated with the formation of a highly vascularized granulation tissue around the graft.

Briefly, six to eight week old NOD/LtSz-Prkdc$^{scid}$/J mice (NOD-SCID; mouse weight about 20–30 g; Jackson Laboratory, Bar Harbor, Me.) were anesthetized with pentobarbital (about 50 mg/kg; Abbott Laboratories, North Chicago, Ill.) intraperitoneally (i.p.) and methoxyflurane (Mallinckrodt Veterinary, Mudelein, Ill.) by inhalation. These mice were housed in a barrier facility to protect them from excessive pathogen exposure. Before injection, the pentobarbital was diluted 1:10 in sterile PBS with about 300 µL being administered per mouse. Extra pentobarbital was prepared in case an additional administration was needed. For methoxyflurane inhalation, cotton lightly soaked with methoxyflurane was placed into a 10 cc syringe lacking the plunger while operating under a hood to avoid methoxyflurane inhalation. The mouse's head then was placed into the open end of the syringe and its breathing monitored. Care was taken to ensure that the mice were not over sedated with methoxyflurane since it can be toxic. Typically, mice were ready to use within five to ten minutes of constant application of methoxyflurane. Once anesthetized, each mouse was placed on its side on sterile gauze or paper towels, and its back region shaved without cutting the skin using sharp scissors. Care was taken to prevent the mice from breathing hair shavings. Once a mouse was shaved, curved forceps were used to pick up the skin and a small incision was made along the dorsal midline. Once cut, one end of the skin was lifted and scissors were slid under the skin to prepare a canal for the implanted tissue. The inflamed human synovial tissue obtained from RA patients was macroscopically cut into equal pieces of about three to four mm in size (about 30–60 cubic mm) and placed in the prepared canal using straight forceps. Curved forceps were used to hold the tissue in place from the outside while the incision was sutured. After removal of the methoxyflurane inhalation, the mice were monitored to ensure recovery. Typically, the mice recovered within five to ten minutes following methoxyflurane removal.

Engraftment of the implanted human synovial tissue generally occurred within seven days. Mice were sacrificed after three weeks, and the synovial tissue was retrieved and embedded in OCT compound (Tissue-Tek, Sakura Finetek, Torrance, Calif.) or shock frozen in liquid nitrogen for future RNA isolation.

Synovial tissue from eleven RA patients was implanted into NOD/LtSz-Prkdc$^{scid}$/J mice. Histomorphology of the human tissue upon explantation revealed that the inflammatory lesions persisted at least three to four weeks. In addition, the number of tissue infiltrating T cells declined initially before reaching a plateau. Before implantation, fresh surgical synovial tissue exhibited a low level of IFN-γ transcription (median copy numbers of 33 per $2 \times 10^6$ β-actin sequences). In addition, the macrophage products IL-1β and TNF-α were detected with median copy numbers of 186 and 295, respectively, per $2 \times 10^6$ β-actin sequences before implantation. After engraftment into NOD/LtSz-Prkdc$^{scid}$/J mice, the human synovial tissue exhibited an elevated level of mRNA synthesis for all three cytokines (FIG. 1). Specifically, two to three weeks after implantation, in situ transcription of IFN-γ, IL-1β, and TNF-α reached median copy numbers of 492, 2580, and 14228, respectively, per $2 \times 10^6$ β-actin sequences. The ten to fifty fold increase in the production of cytokine transcripts in the xenografts was statistically significant (IFN-γ, p=0.002; IL-1β, p=0.002; TNF-α, p=0.01).

The kinetics of enhanced cytokine mRNA synthesis in xenotransplanted rheumatoid synovium were examined by implanting four to eight different mice with fragments of synovial tissue from the same donor. Grafts were successively harvested between one to four weeks following transplantation. Transcription of IFN-γ, IL-1β, and TNF-α reached a maximum two to three weeks after engraftment with changes in IFN-γ transcription closely correlating to those changes observed in IL-1β and TNF-α mRNA production.

Example 2- Generation of Synovial T Cell Lines and Adoptive Transfer Experiments Small pieces (about 10–30 cubic mm) of synovial tissue obtained from RA patients were cultured in 24-well cell culture plates (Costar, Cambridge, Mass.) in RPMI 1640 supplemented with 10% FCS (Summit Biotechnology, Fort Collins, Co.) and 20 IU/mL of rhIL-2 (Cetus, Emeryville, Calif.). Established T cell lines were maintained by weekly polyclonal restimulation with immobilized anti-CD3 antibodies and 20 IU/mL IL-2. CD4$^+$ and CD8$^+$ T cell lines were established from synovial tissue-derived T cells by sorting for CD3$^+$/CD4$^+$ or CD3$^+$/CD8$^+$ cells on a FACSVantage (antibodies and equipment from Becton Dickinson Immunocytometry Systems, San Jose, Calif.).

In adoptive transfer experiments, mice were implanted with human synovial tissue as described in Example 1. Two weeks later, the mice were injected i.p. with 5×10$^7$ unsorted T cells, 2.5×10$^7$ purified CD4$^+$ T cells, or 2.5×10$^7$ purified CD8$^+$ T cells expanded from nonimplanted autologous synovial tissue. Control mice received injections with medium alone. One week after the adoptive transfer, the human synovial tissue was harvested and analyzed. In selected experiments, human synovium-SCID mouse chimeras were adoptively transferred with autologous T cells fourteen days after implantation and were injected i.p. with 250 µg rabbit anti-human IL-16 or normal rabbit IgG (both from Pepro Tech, Rocky Hill, N.J.) on days 17 and 18 following implantation. In these experiments, the synovial tissue was harvested on day 22. To assess the function of adoptively transferred synovial T cells, the in situ transcription of IFN-γ, IL-1β, and TNF-α in the engrafted synovial tissue was semiquantified by PCR (expressed as transcript numbers after being normalized to the number of β-actin transcripts), and the production of cytokine polypeptides in the tissue was examined by immunohistochemistry.

PCR-ELISA was used to determine in situ cytokine transcription in tissue. Briefly, total RNA was extracted from synovial tissue using a commercially available reagent (Trizol; Life Technologies, Grand Island, N.Y.), and cDNA was synthesized using oligo dT and AMV reverse transcriptase (both obtained from Boehringer Mannheim, Indianapolis, Ind.). cDNA from synovial tissue was adjusted to contain equal numbers of β-actin transcripts. Adjusted cDNA was amplified by PCR with cytokine-specific primers under nonsaturating conditions in parallel with a standard containing a known number of cytokine sequences. Amplified products were labeled with digoxygenin 11-dUTP (Boehringer Mannheim) and then semiquantified in a liquid hybridization assay with biotinylated internal probes using an ELISA system (Boehringer Mannheim). The labeled PCR products were hybridized for two hours with 200 ng/mL probe at 42° C. for β-actin, IFN-γ, TGF-β1, and TNF-α, and at 55° C. for IL-1β, IL-10 and IL-16. Details of the assay and sequences of the primers and probes have been published (Klimiuk P A et al., *Am. J. Pathol.* 151:1311–1319 (1997); Weyand C M, et al., *Arthritis Rheum.* 40:19–26 (1997); and Brack A et al., *J. Clin. Invest.* 99:2842–2850 (1997)) except for IL-16 (primers: 5'-AAG CTG ACT CCA GAG CCA TGC C-3' (SEQ ID NO:1) and 5'-TCA GCA TGT CCT GCC TAG G-3' (SEQ ID NO:2); probe: 5'-GGC ACT GCC TGA TGG ACC TGT CAC G-3' (SEQ ID NO:3)). Hybrids were immobilized on streptavidin-coated microtiter plates and, after washing, were detected with a peroxidase-conjugated anti-digoxygenin antibody. The plates were developed by a color reaction using ABTS (2,2'-Azino-di-[3-ethylbenzthiazoline sulfonate, (Cooper S M et al., *Arthritis Rheum.* 34:537–546 (1991)),] diammonium salt) substrate and quantified using a kinetic microplate reader (Molecular Devices, Sunnyvale, Calif.). The number of cytokine-specific sequences was determined by interpolation on a standard curve and was expressed as the number of cytokine sequences per 2×10$^6$ β-actin sequences (Weyand C M, et a., *Arthritis Rheum.* 40:19–26 (1997)).

The following antibodies were used for immunohistochemistry: mouse anti-CD3 mAb (1:100; Becton Dickinson), mouse anti-CD8 mAb (1:5; Becton Dickinson), mouse anti-IFN-γ mAb (1:100; Genzyme Diagnostics, Cambridge, Mass.), rabbit anti-TNF-α mAb (1:250; Genzyme Diagnostics), polyclonal rabbit anti-IL-16 Ab (1:50; PeproTech, Rocky Hill, N.Y.), mouse anti-CD68 mAb (1:250; Dako, Carpinteria, Calif.), biotinylated polyclonal rabbit anti-mouse Ig Ab (1:300; Dako), and polyclonal biotinylated swine anti-rabbit Ig Ab (1:300; Dako). Briefly, synovial tissues embedded in OCT compound were cut into 5 µm sections, mounted onto gel coated slides (Superfrost/Plus, Fisher Scientific, Pittsburgh, Pa.), and dried in a 37° C. desiccator. The slides were then stored at −70° C. Before staining, slides were fixed in acetone for ten minutes, air dried, and fixed in 1% paraformaldehyde/EDTA, pH 7.2, for three minutes. Endogenous peroxidase was blocked with 0.3% $H_2O_2$ in 0.1% sodium azide. Nonspecific binding was blocked with 5% normal goat serum (Life Technologies) for 15 minutes. Sections were stained with primary antibody for 30 minutes at room temperature. After incubation with the appropriate biotinylated secondary reagent, slides were developed with either streptavidin-peroxidase, 1:250 (Dako), and 3,3'-diaminobenzidine tetrahydrochloride (DAB; Sigma Chemical, St. Louis, Mo.), or the VectaStain ABC-AP kit and alkaline phosphatase substrate kit-1 (Vector Laboratories, Burlingame, Calif.). For two-color immunohistochemistry, slides were then washed in 0.5% Triton X-100/PBS for ten minutes. Nonspecific binding was blocked for 15 minutes with 5% normal goat serum, and the sections were stained with a polyclonal rabbit anti-IL-16 antibody for one hour at room temperature. After incubation with biotinylated swine anti-rabbit antibody, slides were developed with the VectaStain ABC-CP kit. Negative controls without primary antibody were processed in parallel. Sections were counter stained with hematoxylin, and permanently mounted in Cytoseal-280 (Stephens Scientific, Riverdale, N.J.).

Figure 2:
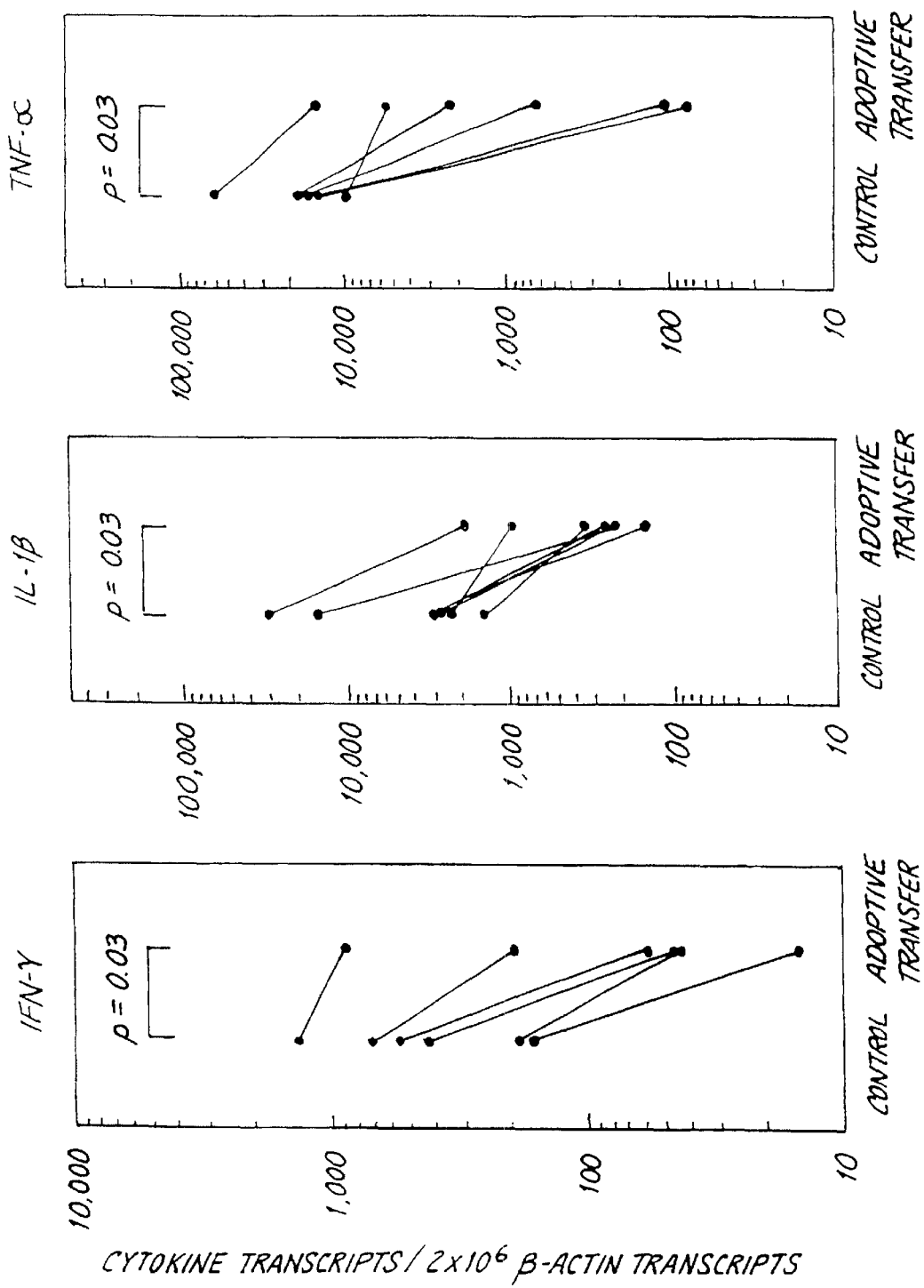
FIG. 2 contains three graphs depicting the level of cytokine mRNA production in human synovial tissue harvested from human synovium-SCID mouse chimeras receiving either medium only (designated control) or autologous synovial tissue-derived T cells (designated adoptive transfer).

Transfer of unsorted tissue-derived T cells had a profound effect on the functional activity of T cells and macrophages in the human graft. Injection of autologous T cells consistently resulted in a significant (p=0.03) suppression of IFN-γ mRNA to ten percent of control levels (FIG. 2). In grafts from control animals, the median tissue concentration was 492 IFN-γ transcripts whereas only 52 copies were detected after adoptive transfer. The transferred cells not only inhibited IFN-γ production, but they also affected IL-1β and TNF-α production. Median tissue concentrations of IL-1β were reduced from 2,974 to 304 transcripts (p=0.03), and TNF-α-specific sequences reduced from 17,301 to 1,454 copies (p=0.03).

Figure 3:
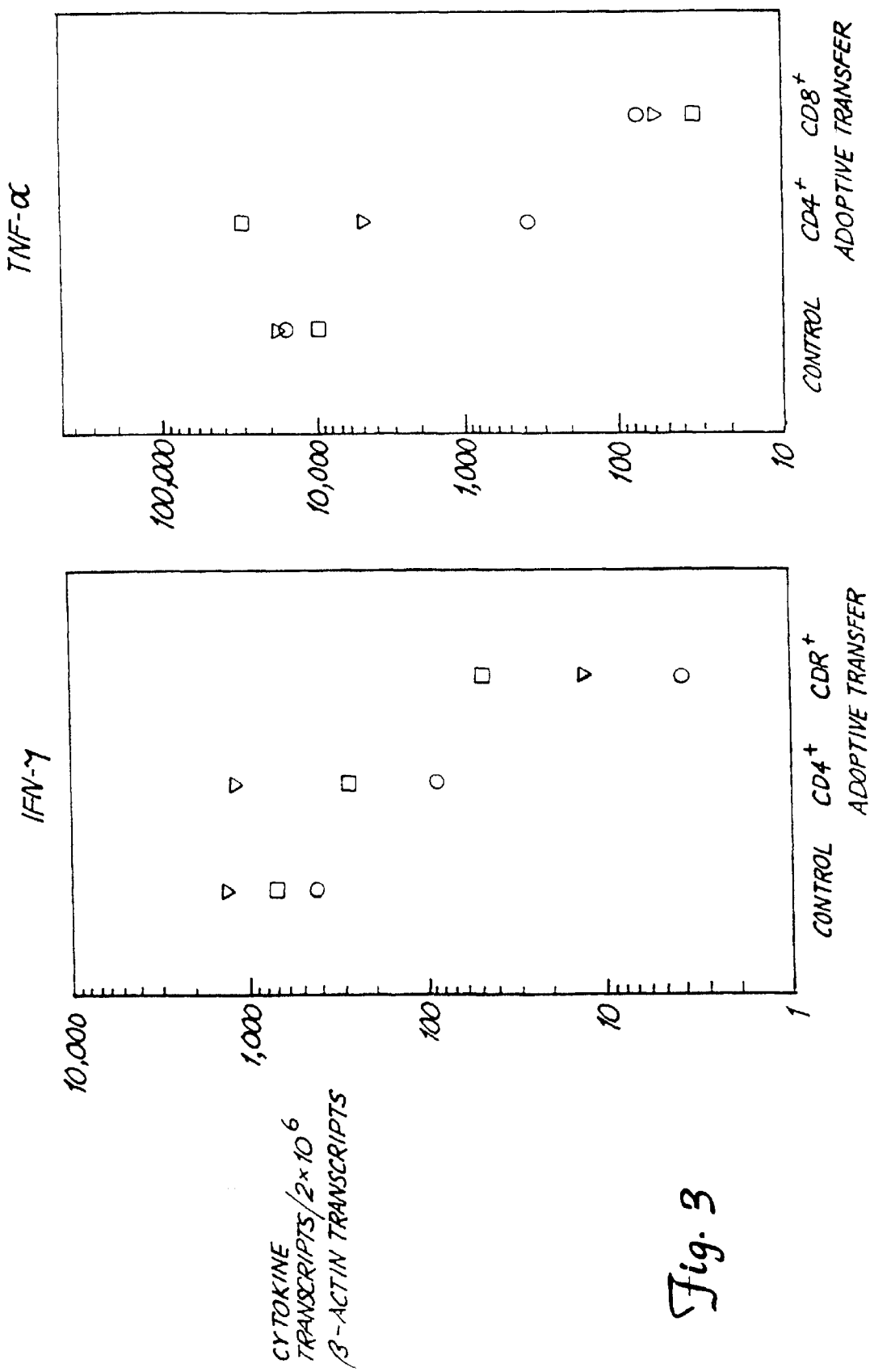
FIG. 3 contains two graphs depicting the level of cytokine mRNA production in human synovial tissue harvested from human synovium-SCID mouse chimeras receiving medium only, autologous CD3$^+$/CD4$^+$ T cells, or autologous CD3$^+$/CD8$^+$ T cells. Identical symbols represent data obtained from tissue originating from the same patient.

To identify the cell subset capable of reducing cytokine production in inflamed synovial tissue, T cell lines were sorted into CD4$^+$ and CD8$^+$ T cell lines, and cells from each of the subsets were adoptively transferred. Following injection of 2.5×10$^7$ autologous CD4$^+$ T cells, synthesis of IFN-γ and TNF-α mRNA in human synovial tissue was essentially unchanged (FIG. 3). Conversely, transfer of 2.5×10$^7$ autologous synovial CD8$^+$ T cells induced profound inhibition of IFN-γ as well as TNF-α transcription (FIG. 3). Control grafts contained a mean of 827 IFN-γ transcripts, whereas the mean copy number was reduced to 21 in synovial tissue retrieved from animals injected with CD8$^+$ T cells (p=0.10). Similarly, minimal TNF-α mRNA was detectable after transfer of CD8$^+$ T cells (56 copies), whereas control tissues expressed a mean of 14,867 copies (p=0.03). In addition, the T cell lines containing CD8+ T cells reduced the transcription of these cytokines to levels similar to the levels detected in fresh human synovial tissue prior to implantation. Similar results were obtained following intravenous administration of autologous sorted and unsorted T cells. These results indicate that CD8+ T cells can accumulate within the implanted human synovial tissue after adoptive transfer into the blood stream or peritoneal cavity.

Figure 4:
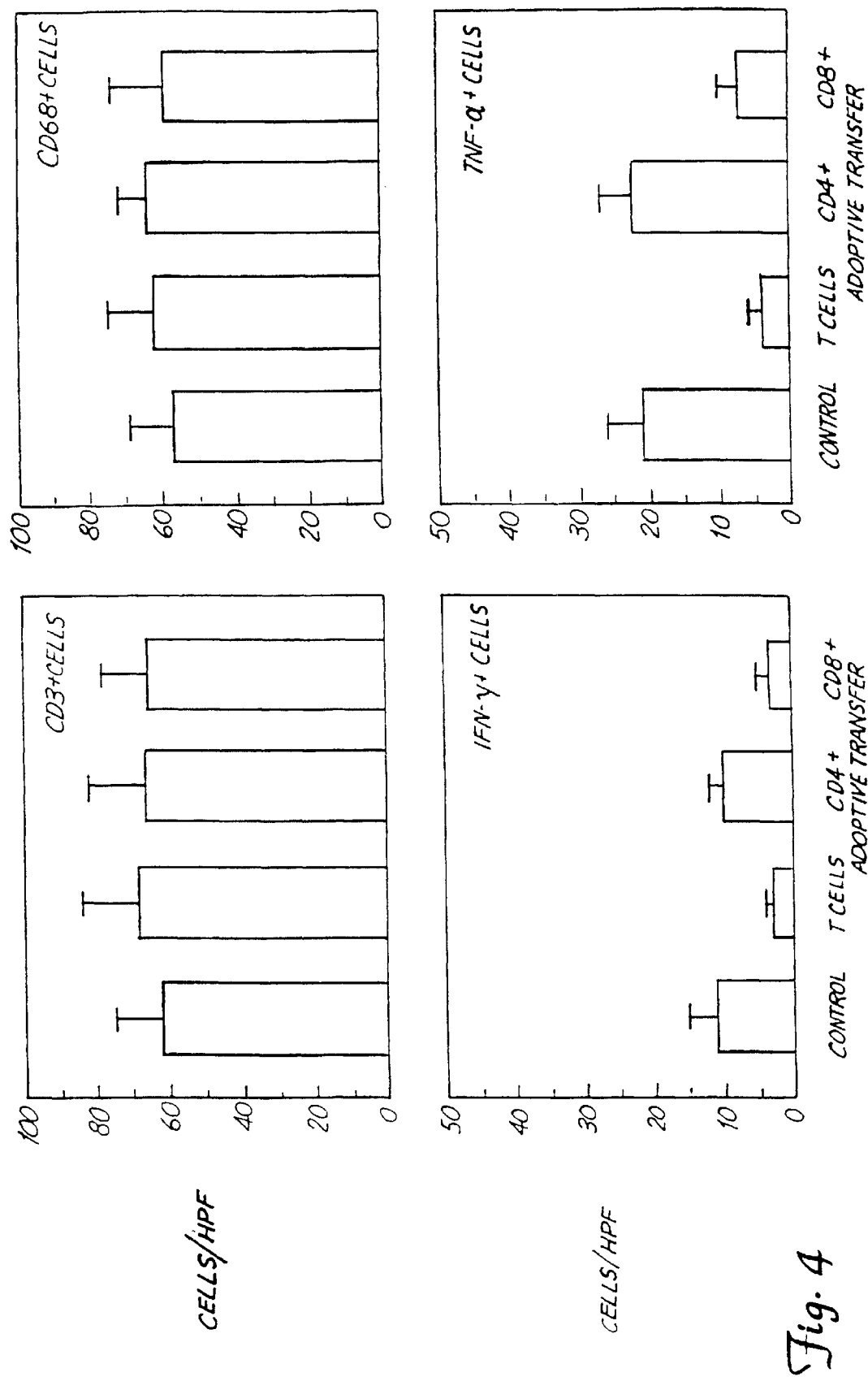
FIG. 4 contains four bar graphs depicting the number of CD3$^+$ cells, CD68$^+$ cells, IFN-γ-producing cells, and TNF-α-producing cells per high power field (hpf) in human synovial tissue harvested from human synovium-SCID mouse chimeras receiving medium only or the designated autologous synovial tissue-derived T cell population.

Immunohistochemical studies of tissue retrieved from human synovium-SCID mouse chimeras demonstrated that the cellularity of the infiltrate was not influenced by the adoptively transferred T cells. Tissue sections were stained with anti-CD3 and anti-CD68 monoclonal antibodies and the numbers of T cells and macrophages per section were counted. The results were generated from three experiments using synovial tissue from three patients. About 60–70 CD3+ T cells and 50–70 CD68+ macrophages per high power field were present in control tissue (FIG. 4). After adoptive transfer of unsorted synovial T cells or sorted CD4+ or CD8+ T cells, the number of tissue-infiltrating CD3+ T cells and CD68+ macrophages did not change. The number of IFN-γ- and TNF-α-producing cells, however, was reduced by about 70 percent after transferring CD8+ T cells. These results indicate that synovial CD8+ T cells downregulate inflammatory activity in rheumatoid synovitis. These results also indicate that the downregulation of T cell and macrophage function is not related to a cytotoxic activity of CD8+ T cells since no cell depletion was observed within synovial lesions.

To determine if the inhibitory activity of adoptively transferred CD8+ T cells was related to the production of a cytokine, expression of IL-16 as well as putative anti-inflammatory cytokines (e.g., IL-4, IL-10, and TGF-β1) in synovial tissue harvested from animals injected with medium only, unsorted synovial T cells, sorted CD4+ T cells, or sorted CD8+ T cells was compared in two separate experiments. Briefly, human tissue grafts were collected from human synovium-SCID mouse chimeras following adoptive transfer, and cDNA prepared so that the production of IL-4, IL-10, IL-16, and TGF-β1 mRNA transcripts could be measured. IL-4 transcripts were not detectable in any harvested tissue. IL-10 transcripts were present at slightly varying amounts without a clear correlation with the type of transferred cell (Table I). However, IL-16 and TGF-β1 transcription inversely correlated with IFN-γ, IL-1β, and TNF-α mRNA production (Table I, and FIGS. 2 and 3). IL-16 transcripts were present in low numbers in control grafts (374 and 461 copies), but this number increased five-fold upon transfer of either unsorted autologous synovium-derived T cells (1910 and 2573 copies) or sorted CD8+ T cells (1564 and 2069 copies). Similar results were obtained for TGF-β1, which revealed a ten-fold increase in transcript number after adoptive transfer of unsorted autologous synovium-derived T cells or sorted CD8+ T cells. Transfer of sorted CD4+ T cells did not alter synthesis of either IL-16 or TGF-β1. These results indicated that IL-16 and TGF-β1 may mediate the downregulatory activity of synovial CD8+ T cells.

TABLE I

Level of cytokine production by human synovial tissue harvested from human synovium-SCID mouse chimeras after adoptive transfer.

| | | Adoptive transfer | | | |
|---|---|---|---|---|---|
| | | Medium Only | Unsorted T cells | CD4+ T cells | CD8+ T cells |
| Experiment 1 | IL-10 | 1437 ± 131* | 1303 ± 139 | 938 ± 28 | 1764 ± 333 |
| | TGF-β1 | 597 ± 72 | 7915 ± 209 | 1045 ± 51 | 4856 ± 183 |
| | IL-16 | 461 ± 60 | 2573 ± 544 | 694 ± 14 | 2069 ± 510 |
| Experiment 2 | IL-10 | 391 ± 14 | 395 ± 70 | 202 ± 20 | 357 ± 22 |
| | TGF-β1 | 145 ± 23 | 9840 ± 854 | 631 ± 107 | 3039 ± 81 |
| | IL-16 | 374 ± 170 | 1910 ± 71 | 427 ± 68 | 1564 ± 375 |

*Number of cytokine transcripts per $2 \times 10^6$ β-actin sequences (mean + SD)

Figure 5:
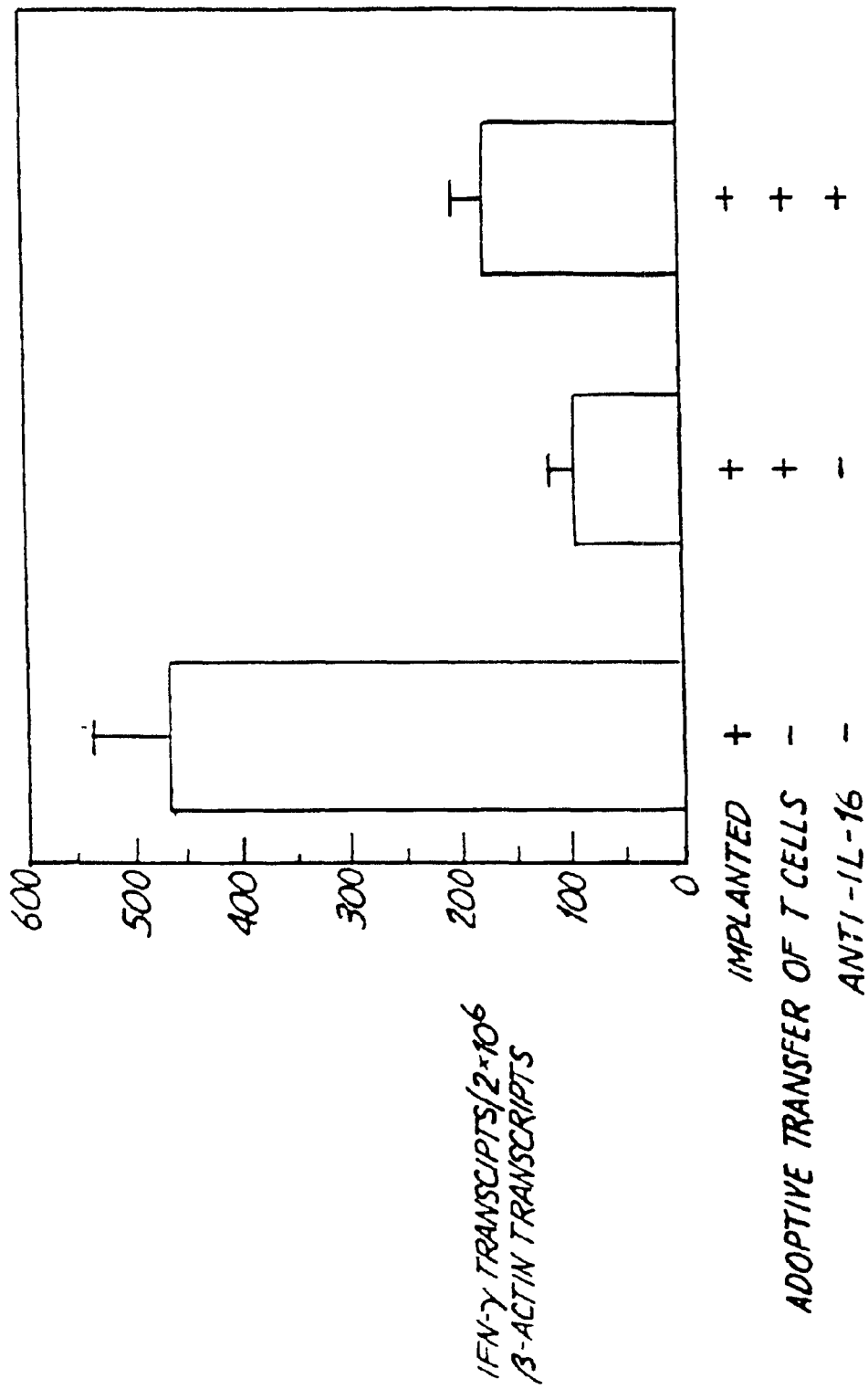
FIG. 5 is a bar graph depicting the level of IFN-γ mRNA production in human synovial tissue harvested from human synovium-SCID mouse chimeras receiving either medium only or autologous synovial tissue-derived T cells as well as either control antibody or anti-IL-16 antibody.

Anti-IL-16 antibody was used to determine if the immunosuppressive effect of adoptively transferred synovial T cells was at least in part related to IL-16 release. Three days after adoptive transfer of $5 \times 10^7$ unsorted autologous T cells, human synovium-SCID mouse chimeras were treated with two consecutive daily doses of anti-IL-16 antibody (250 μg for each dose). Control mice received two consecutive daily doses of normal rabbit immunoglobulin (250 μg for each dose). Four days after antibody treatment, the human synovial tissue was harvested and analyzed. Adoptive transfer of unsorted tissue-derived T cells reduced transcription of IL-1β and IFN-γ to about 15 percent of untreated controls. In three separate experiments, administration of anti-IL-16 antibody partially reversed the T cell-mediated suppression. IFN-α transcription was higher in human synovial tissue harvested from animals receiving anti-IL-16 antibody treatment after adoptive transfer compared to tissue harvested from animals not receiving the anti-IL-16 antibody (FIG. 5). In parallel, administration of anti-IL-16 antibody increased the number of IL-1β transcripts with respect to the level observed in tissue harvested from animals not receiving the anti-IL-16 antibody treatment. Anti-IL-16 antibody treatment did not restore maximal synthesis of either of these pro-inflammatory mediators, suggesting either incomplete neutralization of tissue IL-16 or a contribution of another mediator, e.g. TGF-β1, in the suppression of IFN-γ and IL-1β within tissue.

Figure 6:
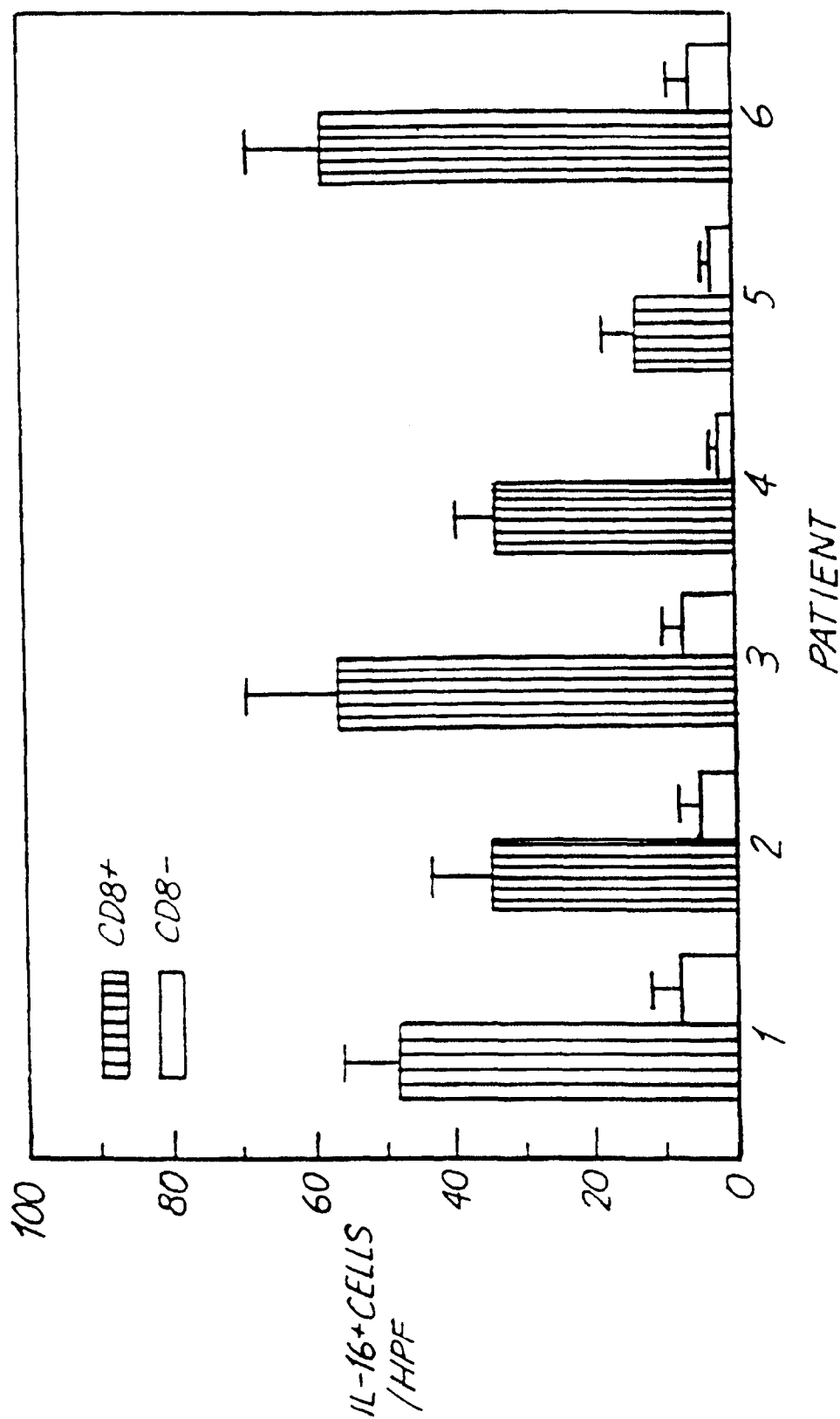
FIG. 6 is a bar graph depicting the number of CD8$^+$/IL-16$^+$ and CD8$^-$/IL-16$^+$ cells per high power field in synovial tissue obtained from six RA patients.

To determine if tissue-infiltrating T cells in rheumatoid synovitis spontaneously synthesized IL-16, immunohistochemical studies were performed. Synovial tissue sections from six RA patients were stained with anti-IL-16 and T cell specific antibodies. IL-16-positive T cells were present in all tissues. By two-color immunohistochemistry, the phenotype of IL-16-producing T cells in the synovium was determined to be predominantly CD8+ (FIG. 6). IL-16 was found in 69–93 percent of all tissue-infiltrating CD8+ T cells. In fact, CD8+ T cells were the predominant source of IL-16 in the synovium. Only 6–19 percent of all synovial cells producing IL-16 were negative for CD8. The small fraction of CD8−/IL-16+ cells in synovial tissue included T cells as well as non-T cells, which were probably synoviocytes. There was a tendency for IL-16-producing CD8+ T cells to be arranged in clusters and to be grouped in areas of T cell enrichment. No particular spatial relationship between CD8+/IL-16+ T cells and TNF-α- and IL-1β-producing CD68+ cells was detected. The total number of CD8+ T cells contributing to the synovial infiltrates varied, suggesting that heterogeneity in rheumatoid synovitis is related to diversity in IL-16-mediated immunoregulation.

Example 3-Treating Inflammation with Recombinant Human IL-16

Human synovium-SCID mouse chimeras were treated with daily i.p. injections of either buffer only or recombinant human IL-16 (rhIL-16; PeproTech) starting on day seven after tissue implantation. Two doses of rhIL-16 (500 ng and 1000 ng per injection) and two treatment durations (10 and 14 days) were tested. For each cytokine dose and each treatment duration, four independent human synovium-SCID mouse chimeras were studied. Implanted tissues were harvested on day 17 for animals treated 10 days, and day 21 for animals treated 14 days. Each harvested tissue was analyzed by immunohistochemistry as well as by PCR-ELISA.

Figure 7:
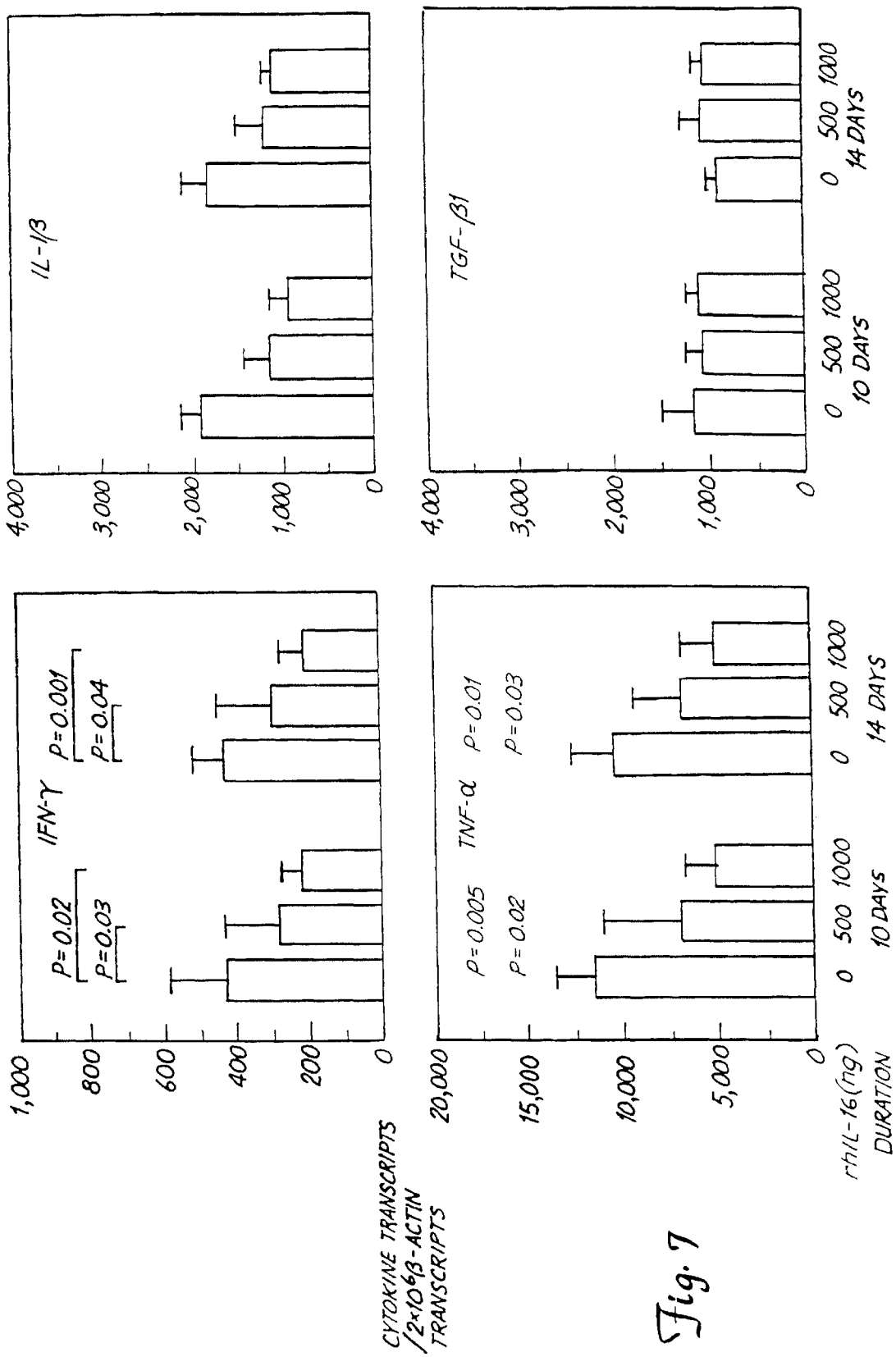
FIG. 7 contains four bar graphs depicting the level of cytokine production in human synovial tissue harvested from human synovium-SCID mouse chimeras receiving treatment with or without recombinant human IL-16 (rhIL-16) for either ten or fourteen days.

Treatment with IL-16 markedly reduced in situ transcription of IFN-γ, IL-1β, and TNF-α (FIG. 7). Reduced transcription of all three pro-inflammatory cytokines was apparent after ten days of treatment with the low dose of 500 ng rhIL-16. The high dose of rhIL-16 (1000 ng) was slightly more effective. IFN-γ, IL-1β, and TNF-α transcripts were all downregulated to about 50 percent of the levels observed in grafts from control mice. The inhibition was significant for all three pro-inflammatory cytokines for both doses and for both treatment durations. Notably, the inhibitory effect of rhIL-16 treatment on cytokine transcription was not a generalized phenomenon. Levels of TGF-β1 and IL-10 mRNA were unaffected by the injection of exogenous rhIL-16. These results indicate that the increased production of TGF-β1 observed after adoptive transfer of $CD8^+$ T cells was not a direct consequence of IL-16 release (FIG. 7).

Figure 8:
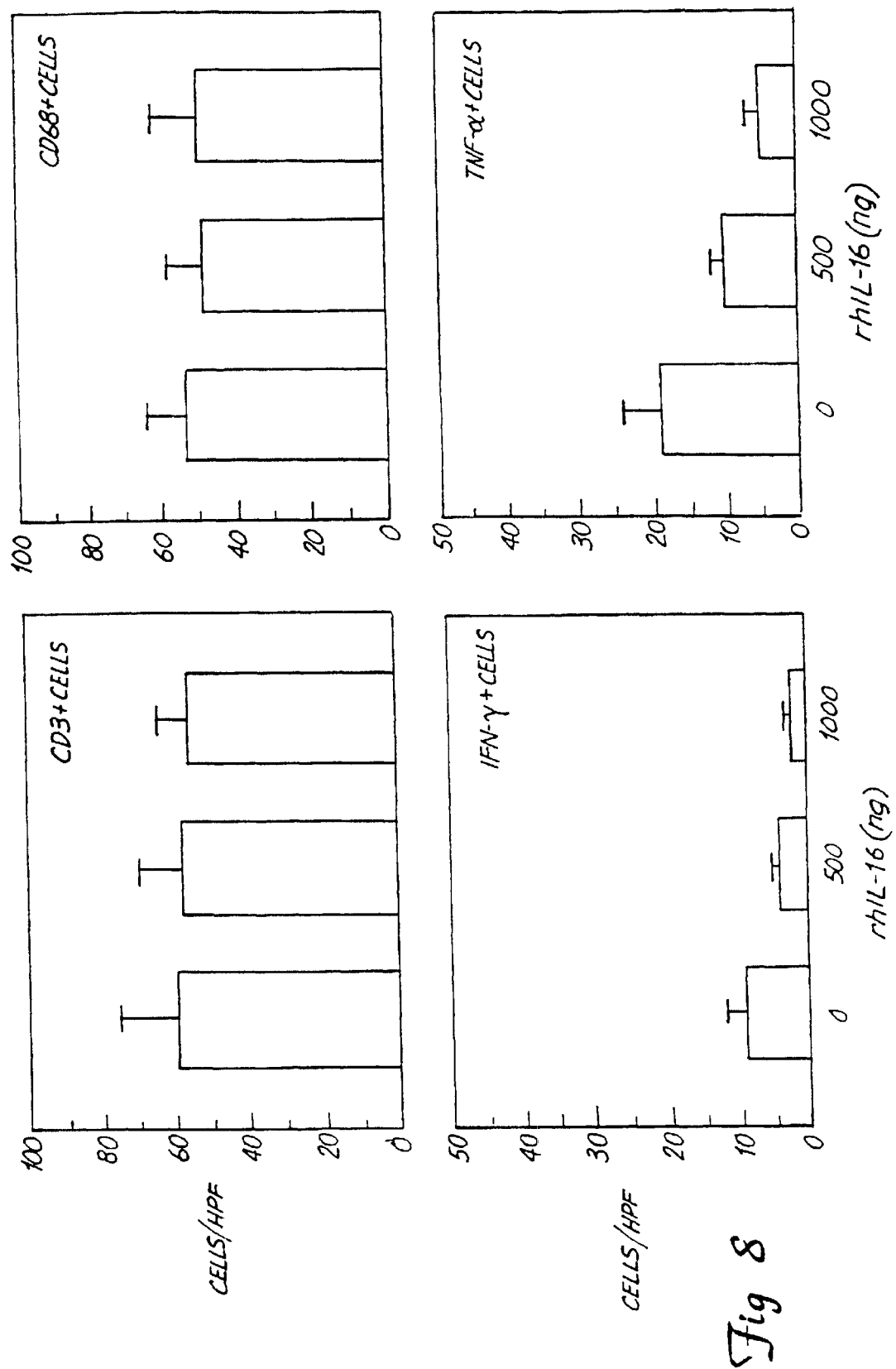
FIG. 8 contains four bar graphs depicting the number of CD3$^+$ cells, CD68$^+$ cells, IFN-γ-producing cells, and TNF-α-producing cells per high power field in human synovial tissue harvested from human synovium-SCID mouse chimeras receiving treatment with or without rhIL-16 for ten days.

To evaluate the effects of exogenous rhIL-16 on the synovial lesions, tissue sections from synovial tissue samples harvested from rhIL-16 treated animals were analyzed. Following treatment with rhIL-16, the microanatomy of the synovial infiltrates was maintained. In addition, the number of tissue-infiltrating $CD3^+$ T cells and $CD68^+$ macrophages was conserved (FIG. 8). Injection of rhIL-16, however, markedly changed the functional activity of IFN-γ- and TNF-α-producing cells. Specifically, rhIL-16 treatment of human synovium-SCID mouse chimeras almost completely reduced IFN-γ and TNF-α production by the cells present within inflammatory lesions.

Taken together, the data presented herein indicates that the paradoxical functional silence of tissue infiltrating T cells in RA results from in situ inhibition of cellular function by anti-inflammatory mechanisms mediated in part by IL-16. In other words, physiologic regulatory pathways are in place that can suppress inflammatory synovitis. In fact, the in vivo results presented herein indicate that boosting CD8-directed immunosuppression could eradicate synovial inflammation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating an inflammatory disease, said method comprising:
   a) identifying a host in need of an anti-inflammatory treatment, wherein said host has inflamed tissue, and
   b) administering a pharmaceutically effective amount of an IL-16 polypeptide or an IL-16-mimicking molecule to said host under conditions such that the expression of an inflammatory cytokine in the region of said inflamed tissue is reduced.

2. The method of claim 1, wherein said inflammatory disease is rheumatoid arthritis.

3. The method of claim 1, wherein said IL-16-mimicking molecule comprises a recombinant HIV gp120 polypeptide.

4. The method of claim 1, wherein said method comprises administering, to said host, a polypeptide selected from the group consisting of TGF-β1, IL-4 and IL-10.

5. The method of claim 1, wherein said inflammatory cytokine comprises a cytokine selected from the group consisting of IFN-γ, IL-1β, and TNF-α.

6. The method of claim 1, wherein said IL-16 polypeptide is recombinant human IL-16.

7. The method of claim 1, wherein said host is a mammal.

8. The method of claim 7, wherein said mammal is a human.

9. A method of treating an inflammatory disease in a host, said method comprising providing nucleic acid to said host, wherein said nucleic acid encodes an IL-16 polypeptide and wherein said host expresses said IL-16 polypeptide from said nucleic acid such that the expression of an inflammatory cytokine is reduced in said host.

10. The method of claim 9, wherein said inflammatory disease is rheumatoid arthritis.

11. The method of claim 9, wherein said method comprises providing a second nucleic acid to said host, wherein said second nucleic acid encodes an immunosuppressive cytokine.

12. The method of claim 11, wherein said immunosuppressive cytokine comprises a cytokine selected from the group consisting of TGF-β1, IL-4, and IL-10.

13. The method of claim 9, wherein said inflammatory cytokine comprises a cytokine selected from the group consisting of IFN-γ, IL-1β, and TNF-α.

14. The method of claim 9, wherein said IL-16 polypeptide is human IL-16.

15. The method of claim 9, wherein said host is a mammal.

16. The method of claim 15, wherein said mammal is a human.

17. A pharmaceutical composition for treating an inflammatory disease in a host, said composition comprising an IL-16 polypeptide or an IL-16-mimicking molecule and an immunosuppressive cytokine, wherein the administration of said composition to said host reduces the expression of an inflammatory cytokine in said host.

18. The composition of claim 17, wherein said inflammatory disease is rheumatoid arthritis.

19. The composition of claim 17, wherein said IL-16 polypeptide is recombinant human IL-16.

20. The composition of claim 17, wherein said IL-I16-mimicking molecule comprises a recombinant HIV gp120 polypeptide.

21. The composition of claim 17, wherein said immunosuppressive cytokine comprises a cytokine selected from the group consisting of TGF-β1, IL-4, and IL-10.

22. The composition of claim 17, wherein said inflammatory cytokine comprises a cytokine selected from the group consisting of IFN-γ, IL-1β, and TNF-α.

23. The composition of claim 17, wherein said host is a mammal.

24. The composition of claim 23, wherein said mammal is a human.

25. An article of manufacture comprising packaging material and an IL-16 polypeptide or IL-16-mimicking molecule, wherein said packaging material comprises a label or package insert indicating that said IL-16 polypeptide or IL-16-mimicking molecule can be administered to a host for the purpose of treating an inflammatory disease.

26. An article of manufacture comprising packaging material and nucleic acid encoding an IL-16 polypeptide, wherein said packaging material comprises a label or package insert indicating that said nucleic acid can be administered to a host for the purpose of treating an inflammatory disease.

27. The use of an IL-16 polypeptide or an IL-16-mimicking molecule in the manufacture of a medicament for treating an inflammatory disease in a host in need of an anti-inflammatory treatment, wherein said host has inflamed tissue, and wherein administering a pharmaceutically effective amount of said medicament to said host reduces the expression of an inflammatory cytokine in the region of said inflamed tissue.

28. The use of cells in the manufacture of a medicament for treating an inflammatory disease in a host in need of an anti-inflammatory treatment, wherein said host has inflamed tissue, and wherein administering said medicament to said host reduces the expression of an inflammatory cytokine in the region of said inflamed tissue.

* * * * *

UNITED STATES PATENT AND TRADEMARK OFFICE
CERTIFICATE OF CORRECTION

PATENT NO. : 6,455,497 B1 Page 1 of 1
DATED : September 24, 2002
INVENTOR(S) : Jorg J. Goronzy, M.D., Ph.D. and Cornelia M. Weyand, M.D., Ph. D.

It is certified that error appears in the above-identified patent and that said Letters Patent is hereby corrected as shown below:

<u>Title page,</u>
After Item [87], PCT Publ. No.: WO99/48514 and PCT Pub. Date: Sep. 30, 1999, please insert the following:
-- Related U.S. Application Data, [60] Provisional Application No. 60/079,282, filed on March 25, 1998. --
Item [57], ABSTRACT,
Line 5, please delete "IL-" and insert -- IL-1β -- therefor.

<u>Column 20,</u>
Line 53, please delete "IL-I16" and insert -- IL-16 -- therefor.

Signed and Sealed this

Nineteenth Day of August, 2003

JAMES E. ROGAN
*Director of the United States Patent and Trademark Office*